US008939966B2

(12) United States Patent  
Hahn

(10) Patent No.: US 8,939,966 B2  
(45) Date of Patent: Jan. 27, 2015

(54) DIFFERENTIAL LASER-INDUCED PERTURBATION (DLIP) FOR BIOIMAGING AND CHEMICAL SENSING

(75) Inventor: David Worthington Hahn, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 475 days.

(21) Appl. No.: 13/056,396

(22) PCT Filed: Aug. 21, 2009

(86) PCT No.: PCT/US2009/054611  
§ 371 (c)(1),  
(2), (4) Date: Jan. 28, 2011

(87) PCT Pub. No.: WO2010/022330  
PCT Pub. Date: Feb. 25, 2010

(65) Prior Publication Data  
US 2011/0137179 A1  Jun. 9, 2011

Related U.S. Application Data

(60) Provisional application No. 61/090,670, filed on Aug. 21, 2008.

(51) Int. Cl.  
    *A61B 18/18*     (2006.01)  
    *G01N 21/64*     (2006.01)  
    *G01N 21/63*     (2006.01)  
    *G01N 21/65*     (2006.01)  
(52) U.S. Cl.  
    CPC .......... *G01N 21/6456* (2013.01); *G01N 21/631* (2013.01); *G01N 21/6408* (2013.01); *G01N 21/65* (2013.01)

USPC .......... 606/10; 606/9; 606/2; 607/88; 607/89; 600/476

(58) Field of Classification Search  
None  
See application file for complete search history.

(56) References Cited

U.S. PATENT DOCUMENTS

| | | | | | |
|---|---|---|---|---|---|
| 4,273,535 | A | * | 6/1981 | Yamamoto et al. | 433/216 |
| 4,784,135 | A | * | 11/1988 | Blum et al. | 606/3 |
| 5,108,388 | A | * | 4/1992 | Trokel | 606/5 |
| 5,252,834 | A | * | 10/1993 | Lin | 250/458.1 |
| 5,394,411 | A | * | 2/1995 | Milchberg et al. | 372/5 |
| 5,435,724 | A | * | 7/1995 | Goodman et al. | 433/215 |
| 5,507,287 | A | * | 4/1996 | Palcic et al. | 600/317 |
| 5,527,350 | A | * | 6/1996 | Grove et al. | 607/89 |
| 5,579,773 | A | * | 12/1996 | Vo-Dinh et al. | 600/317 |
| 5,590,660 | A | * | 1/1997 | MacAulay et al. | 600/478 |
| 5,611,795 | A | * | 3/1997 | Slatkine et al. | 606/9 |

(Continued)

OTHER PUBLICATIONS

Alencar, H., et al., "Colonic Adenocarcinomas: Near-Infrared Microcatheter Imaging of Smart Probes for Early Detection—Study in Mice," *Radiology*, Jul. 2007, pp. 232-238, vol. 244, No. 1.

(Continued)

*Primary Examiner* — Nicholas Evoy  
(74) *Attorney, Agent, or Firm* — Saliwanchik, Lloyd & Eisenschenk

(57) ABSTRACT

Methods for imaging or optical sensing of a material are provided. A first fluorescent image or optical signal of a material can be recorded, the material can be perturbed, and then a second fluorescent image or optical signal of the material can be recorded. The two fluorescent images or signals can be subtracted to give a differential image or optical signal.

80 Claims, 12 Drawing Sheets

(56) References Cited

U.S. PATENT DOCUMENTS

| | | | |
|---|---|---|---|
| 5,647,368 A * | 7/1997 | Zeng et al. ................. 600/476 |
| 5,759,200 A * | 6/1998 | Azar .............................. 607/89 |
| 5,769,792 A * | 6/1998 | Palcic et al. ................. 600/477 |
| 5,782,822 A * | 7/1998 | Telfair et al. ................... 606/5 |
| 5,827,190 A * | 10/1998 | Palcic et al. ................. 600/476 |
| 5,860,967 A * | 1/1999 | Zavislan et al. ............... 606/9 |
| 6,090,102 A * | 7/2000 | Telfair et al. ................. 606/10 |
| 6,095,982 A * | 8/2000 | Richards-Kortum et al. 600/476 |
| 6,165,170 A * | 12/2000 | Wynne et al. ................. 606/9 |
| 6,166,385 A * | 12/2000 | Webb et al. ............... 250/458.1 |
| 6,302,876 B1 * | 10/2001 | Shimmick et al. ............. 606/5 |
| 6,344,653 B1 * | 2/2002 | Webb et al. ............... 250/458.1 |
| 6,403,332 B1 * | 6/2002 | Bearman et al. ................ 435/29 |
| 6,436,127 B1 * | 8/2002 | Anderson et al. .............. 607/89 |
| 6,447,503 B1 * | 9/2002 | Wynne et al. ................... 606/9 |
| 6,520,958 B1 * | 2/2003 | Shimmick et al. ............ 606/10 |
| 6,569,157 B1 * | 5/2003 | Shain et al. .................... 606/12 |
| 6,605,081 B1 * | 8/2003 | Shimmick et al. ............ 606/10 |
| 6,697,666 B1 * | 2/2004 | Richards-Kortum et al. 600/478 |
| 6,713,772 B2 * | 3/2004 | Goodman et al. .......... 250/492.1 |
| 6,736,833 B2 * | 5/2004 | Coleman ....................... 607/94 |
| 6,750,036 B2 * | 6/2004 | Bearman et al. ................ 435/29 |
| 6,816,520 B1 * | 11/2004 | Tulloch et al. ................. 372/22 |
| 6,904,073 B2 * | 6/2005 | Yager et al. .................... 372/57 |
| 6,963,591 B2 * | 11/2005 | Tulloch et al. ................. 372/22 |
| 6,984,228 B2 * | 1/2006 | Anderson et al. ................ 606/9 |
| 7,090,669 B2 * | 8/2006 | Van Saarloos .................. 606/5 |
| 7,144,248 B2 * | 12/2006 | Irwin ............................. 433/29 |
| 7,207,983 B2 * | 4/2007 | Hahn et al. ...................... 606/5 |
| 7,221,455 B2 * | 5/2007 | Chediak et al. ............... 356/419 |
| 7,276,059 B2 * | 10/2007 | Irwin ................................ 606/9 |
| 7,316,899 B2 * | 1/2008 | McDevitt et al. ............ 435/6.19 |
| 7,336,989 B2 * | 2/2008 | Chuck et al. ................. 600/477 |
| 7,372,056 B2 * | 5/2008 | Bykanov et al. .......... 250/504 R |
| 7,373,254 B2 * | 5/2008 | Pierce ............................. 702/19 |
| 7,417,211 B2 * | 8/2008 | Nakata et al. .............. 250/201.3 |
| 7,524,316 B2 * | 4/2009 | Hennings et al. ................ 606/7 |
| 7,921,853 B2 * | 4/2011 | Fiset .............................. 128/898 |
| 8,143,600 B2 * | 3/2012 | Seibel et al. ............... 250/461.2 |
| 8,160,680 B2 * | 4/2012 | Boyden et al. ................ 600/476 |
| 8,180,436 B2 * | 5/2012 | Boyden et al. ................ 600/476 |
| 8,323,220 B2 * | 12/2012 | Babaev ............................ 601/2 |
| 2002/0133146 A1 * | 9/2002 | Telfair et al. .................... 606/5 |
| 2002/0146682 A1 * | 10/2002 | Bearman et al. .................. 435/4 |
| 2002/0183811 A1 * | 12/2002 | Irwin .............................. 607/94 |
| 2003/0045916 A1 * | 3/2003 | Anderson et al. .............. 607/89 |
| 2003/0186228 A1 * | 10/2003 | McDevitt et al. ................ 435/6 |
| 2004/0053322 A1 * | 3/2004 | McDevitt et al. ............. 435/7.1 |
| 2004/0102765 A1 * | 5/2004 | Koenig ............................ 606/5 |
| 2004/0199079 A1 * | 10/2004 | Chuck et al. .................. 600/477 |
| 2004/0248144 A1 * | 12/2004 | Mir ................................ 435/6 |
| 2005/0015124 A1 * | 1/2005 | Irwin .............................. 607/94 |
| 2005/0094682 A1 * | 5/2005 | Tulloch et al. ................. 372/22 |
| 2005/0157301 A1 * | 7/2005 | Chediak et al. ............... 356/417 |
| 2005/0177208 A1 * | 8/2005 | Irwin .............................. 607/94 |
| 2005/0197655 A1 * | 9/2005 | Telfair et al. .................... 606/5 |
| 2006/0004306 A1 * | 1/2006 | Altshuler et al. ................ 601/3 |
| 2006/0004347 A1 * | 1/2006 | Altshuler et al. ................ 606/4 |
| 2006/0020309 A1 * | 1/2006 | Altshuler et al. .............. 607/88 |
| 2006/0058712 A1 * | 3/2006 | Altshuler et al. .............. 601/15 |
| 2006/0085053 A1 * | 4/2006 | Anderson et al. .............. 607/94 |
| 2006/0247608 A1 * | 11/2006 | Hahn et al. ...................... 606/5 |
| 2006/0262903 A1 * | 11/2006 | Diebold ........................ 378/62 |
| 2006/0276862 A1 * | 12/2006 | Irwin .............................. 607/94 |
| 2007/0178602 A1 * | 8/2007 | Wolleschensky et al. ..... 436/172 |
| 2007/0282402 A1 * | 12/2007 | Irwin .............................. 607/88 |
| 2008/0058587 A1 * | 3/2008 | Boyden et al. ................ 600/104 |
| 2008/0058649 A1 * | 3/2008 | Boyden et al. ................ 600/476 |
| 2008/0058785 A1 * | 3/2008 | Boyden et al. ................ 606/13 |
| 2008/0058786 A1 * | 3/2008 | Boyden et al. ................ 606/13 |
| 2008/0058788 A1 * | 3/2008 | Boyden et al. ................ 606/14 |
| 2008/0058795 A1 * | 3/2008 | Boyden et al. ................ 606/34 |
| 2008/0059070 A1 * | 3/2008 | Boyden et al. .................. 702/1 |
| 2008/0132886 A1 * | 6/2008 | Cohen et al. .................. 606/34 |
| 2008/0172047 A1 * | 7/2008 | Altshuler et al. ................ 606/9 |
| 2008/0183162 A1 * | 7/2008 | Altshuler et al. ................ 606/9 |
| 2009/0101815 A1 * | 4/2009 | Ohtsuka ........................ 250/307 |
| 2010/0255523 A1 * | 10/2010 | Mik et al. ........................ 435/29 |
| 2011/0181191 A1 * | 7/2011 | Smith et al. .................... 315/149 |
| 2011/0253909 A1 * | 10/2011 | Himmelhaus et al. ..... 250/492.1 |
| 2011/0300504 A1 * | 12/2011 | Kasenbacher ................. 433/29 |

OTHER PUBLICATIONS

Alfano, R.R., et al., "Advances in Optical Imaging of Biomedical Media," *Annals of the New York Academy of Sciences*, May 1997, pp. 248-270, vol. 820, No. 1.

Alfano, R.R., et al., "Laser Induced Fluorescence Spectroscopy from Native Cancerous and Normal Tissue," *IEEE Journal of Quantum Electronics*, Dec. 1984, pp. 284-291, vol. 20, No. 12.

Andersson-Engels, S., et al., "In Vivo Fluorescence Imaging for Tissue Diagnostics," *Physics in Medicine and Biology*, May 1997, pp. 815-824, vol. 42, No. 5.

Arens, C., et al., "Indirect Fluorescence Laryngoscopy in the Diagnosis of Precancerous and Cancerous Laryngeal Lesions," *European Archives of Oto-Rhino-Laryngology*, Jun. 2007, pp. 621-626, vol. 264, No. 6.

Benaron, D.A., et al., "Optical Time-of-Flight and Absorbance Imaging of Biologic Media," *Science*, 1993, pp. 1463-1466, vol. 259, No. 5100.

Brookner, C., et al., "Effects of Biographical Variables on Cervical Fluorescence Emission Spectra," *Journal of Biomedical Optics*, Jul. 2003, pp. 479-483, vol. 8, No. 3.

Chaerle, L., et al., "Seeing Is Believing: Imaging Techniques to Monitor Plant Health," *Biochimica et Biophysica Acta*, 2001, pp. 153-166, vol. 1519, No. 3.

Chance, B., "Near-Infrared Images Using Continuous, Phase-Modulated, and Pulsed Light with Quantitation of Blood and Blood Oxygenation," *Annals of the New York Academy of Sciences*, Feb. 1998, pp. 29-45, vol. 838, No. 1.

Chwirot, B.W., "Spectrally Resolved Fluorescence Imaging of Human Colonic Adenomas," *Journal of Photochemistry and Photobiology B: Biology*, 1999, pp. 174-183, vol. 50, Nos. 2-3.

Contag, P.R., et al., "Bioluminescent Indicators in Living Mammals," *Nature Medicine*, Feb. 1998, pp. 245-247, vol. 4, No. 2.

Corlu, A., et al., "Three-Dimensional In Vivo Fluorescence Diffuse Optical Tomography of Breast Cancer in Humans," *Optics Express*, May 2007, pp. 6696-6716, vol. 15, No. 11.

De Veld, D.C.G., et al., "The Status of In Vivo Autofluorescence Spectroscopy and Imaging for Oral Oncology," *Oral Oncology*, Feb. 2005, pp. 117-131, vol. 41, No. 2.

Emmert-Buck, M.R., at al., "Increased Gelatinase A (MMP-2) and Cathepsin B Activity in Invasive Tumor Regions of Human Colon Cancer Samples," *American Journal of Pathology*, Dec. 1994, pp. 1285-1290, vol. 145, No. 6.

Fisher, B.T., et al., "Development and Numerical Solution of a Mechanistic Model for Corneal Tissue Ablation with the 193 nm Argon Fluoride Excimer Laser," *Journal of the Optical Society of America A: Optics, Image Science and Vision*, Feb. 2007, pp. 265-277, vol. 24, No. 2.

Fisher, B.T., at al., "Measurement of Small-Signal Absorption Coefficient and Absorption Cross Section of Collagen for 193-nm Excimer Laser Light and the Role of Collagen in Tissue Ablation," *Applied Optics*, Oct. 2004, pp. 5443-5451, vol. 43, No. 29.

Fogt, F., et al., "Distinction Between Dysplasia-Associated Lesion or Mass (DALM) and Adenoma in Patients with Ulcerative Colitis," *Human Pathology*, Mar. 2000, pp. 288-291, vol. 31, No. 3.

Funovics, M.A., et al., "Catheter-Based In Vivo Imaging of Enzyme Activity and Gene Expression: Feasibility Study in Mice," *Radiology*, Jun. 2004, pp. 659-666, vol. 231, No. 3.

Goldsmith, J.E.M., et al., "Photochemical Effects in Multiple Species Fluorescence Imaging in Hydrogen-Nitrous Oxide Flames," *Applied Optics*, Nov. 1990, pp. 4852-4859, vol. 29, No. 33.

Haringsma, J., et al., "Fluorescence and Autofluorescence," *Bailliere's Clinical Gastroenterology*, Apr. 1999, pp. 1-10, vol. 13, No. 1.

Haussinger, K., et al., "Autofluorescence Bronchoscopy with White Light Bronchoscopy Compared with White Light Bronchoscopy

(56) References Cited

OTHER PUBLICATIONS

Alone for the Detection of Precancerous Lesions: A European Randomized Controlled Multicentre Trial," *Thorax*, Jun. 2005, pp. 496-503, vol. 60, No. 6.
Hurlstone, D.P., et al., "Techniques for Targeting Screening in Ulcerative Colitis," *Postgraduate Medical Journal*, Jul. 2007, pp. 451-460, vol. 83, No. 981.
Kioi, M., et al., "Matrilysin (MMP-7) Induces Homotypic Adhesion of Human Colon Cancer Cells and Enhances Their Metastatic Potential in Nude Mouse Model," *Oncogene*, Nov. 2003, pp. 8662-8670, vol. 22, No. 54.
Loo, L.-H., et al., "Image-Based Multivariate Profiling of Drug Responses from Single Cells," *Nature Methods*, May 2007, pp. 445-453, vol. 4, No. 5.
Mahadevan, A., et al., "Study of the Fluorescence Properties of Normal and Neoplastic Human Cervical Tissue," *Lasers in Surgery and Medicine*, 1993, pp. 647-655, vol. 13, No. 6.
Mahmood, U., et al., "Near-Infrared Optical Imaging of Protease Activity for Tumor Detection," *Radiology*, Dec. 1999, pp. 866-870, vol. 213, No. 3.
Manoharan, R., et al., "Raman Spectroscopy and Fluorescence Photo Migration for Breast Cancer Diagnosis and Imaging," *Photochemistry and Photobiology*, Jan. 1998, pp. 15-22, vol. 67, No. 1.
Martin, S.F., et al., "Fluorescence Spectroscopy of an In Vitro Model of Human Cervical Precancer Identifies Neoplastic Phenotype," *International Journal of Cancer*, May 2007, pp. 1964-1970, vol. 120, No. 9.
Ramanujam, N., et al., "Cervical Precancer Detection Using a Multivariate Statistical Algorithm Based on Laser-Induced Fluorescence Spectra at Multiple Excitation Wavelengths," *Photochemistry and Photobiology*, Oct. 1996, pp. 720-735, vol. 64, No. 4.
Rembacken, J., et al., "Flat and Depressed Colonic Neoplasms: A Prospective Study of 1000 Colonoscopies in the UK," *The Lancet*, Apr. 2000, pp. 1211-1214, vol. 355.
Rex, D.K., et al., "Colonoscopic Miss Rates of Adenomas Determined by Back-to-Back Colonoscopies," *Gastroenterology*, Jan. 1997, pp. 24-28, vol. 112, No. 1.
Riddell, R.H., et al., "Dysplasia in Inflammatory Bowel Disease: Standardized Classification with Provisional Clinical Implications," *Human Pathology*, Nov. 1983, pp. 931-968, vol. 14, No. 11.
Slovak, M.L., et al., "Simultaneous Detection of Multiple Genetic Aberrations in Single Cells by Spectral Fluorescence in Situ Hybridization," *Cancer Research*, Feb. 2001, pp. 831-836, vol. 61, No. 3.
Sokolov, K., et al., "Optical Systems for In Vivo Molecular Imaging of Cancer," *Technology in Cancer Research and Treatment*, Dec. 2003, pp. 491-504, vol. 2, No. 6.
Srinivasan, R., et al., "Photochemical Cleavage of a Polymeric Solid: Details of the Ultraviolet Laser Ablation of Poly(methyl methacrylate) at 193 and 248 nm," *Macromolecules*, Mar. 1986, pp. 916-921, vol. 19, No. 3.
Stephens, D.J., et al., "Light Microscopy Techniques for Live Cell Imaging," *Science*, Apr. 2003, pp. 82-86, vol. 300, No. 5616.
Sutcliffe, E., et al., "Dynamics of UV Laser Ablation of Organic Polymer Surfaces," *Journal of Applied Physics*, Nov. 1986, pp. 3315-3322, vol. 60, No. 9.
Tearney, G.J., et al., "In Vivo Endoscopic Optical Biopsy with Optical Coherence Tomography," *Science*, Jun. 1997, pp. 2037-2039, vol. 276, No. 5321.
Utzinger, U., et al., "Near-Infrared Raman Spectroscopy for In Vivo Detection of Cervical Precancers," *Applied Spectroscopy*, Aug. 2001, pp. 955-959, vol. 55, No. 8.
Vo-Dinh, T., at al., "Laser-Induced Differential Fluorescence for Cancer Diagnosis Without Biopsy," *Applied Spectroscopy*, Jan. 1997, pp. 58-63, vol. 51, No. 1.
Waggoner, S.E., "Cervical Cancer," *The Lancet*, Jun. 2003, pp. 2217-2225, vol. 361.
Arnold, N., et al. "Model for Laser-Induced Thermal Degradation and Ablation of Polymers," *Applied Physics A*, Jun. 1999, vol. 68, No. 6, pp. 615-625.
Vogel, A., et al., "Mechanisms of Pulsed Laser Ablation of Biological Tissues," *Chemical Reviews*, May 2003, vol. 103, No. 5, pp. 577-644.

\* cited by examiner

DIFFERENTIAL LASER-INDUCED PERTURBATION (DLIP) FOR BIOIMAGING AND CHEMICAL SENSING

CROSS-REFERENCE TO RELATED APPLICATIONS

The present application is the U.S. National Stage Application of International Patent Application No. PCT/US2009/054611, filed on Aug. 21, 2009, which claims the benefit of U.S. Provisional Application Ser. No. 61/090,670, filed Aug. 21, 2008, both of which are hereby incorporated by reference herein in their entirety, including any figures, tables, or drawings.

BACKGROUND OF INVENTION

In general, fluorescence involves the absorption of light (i.e., a photon or photons) by a molecule (i.e., a chromophore), thereby promoting the absorbing chromophore to an excited electronic state. After excitation by the incident photon, the chromophore typically undergoes an internal redistribution of energy, followed by a radiative decay back to the ground state. The internal redistribution of energy can be via a number of processes, such as, vibrational relaxation. Because energy is lost during the internal relaxation processes, the light released during the final radiative decay process is red-shifted to longer wavelengths.

The fluorescence process is an inelastic process characterized by a difference in the incident and the emitted wavelengths. The incident wavelength can be that of excitation or input light, and the emitted wavelength can be that of fluorescence or output light. FIG. 1A depicts an absorption and relaxation process of fluorescence.

Fluorescence techniques have been used as a method of cancer screening. Cancer remains one of the most lethal diseases in the world, and cancer screening and early interdiction are very important tools in reducing cancer-related deaths. Cervical cancer, colorectal cancer, oral cancer, and skin cancers strike millions each year. S. E. Waggoner, *Cervical Cancer*, Lancet, 361:2217-2225 (2003). With these cancer types in particular, the potential benefits of improved screening are enormous. These cancers are invariably preceded by dysplastic precancerous cellular changes, in which histological changes associated with malignancy are often confined to the epithelial layer. C. S. Herrington, M. Wells, *Premalignant and malignant squamous lesions of the cervix*, In H. Fox, M. Wells (eds), Haines and Taylor obstetrical and gynecological pathology, 5$^{th}$ edition, Edinburgh: Churchill Livingstone, pp. 297-338 (2002). Dysplasia, i.e., unequivocal neoplastic epithelium, is commonly relied on as a biomarker of malignancy. R. H. Riddell et al., *Dysplasia in inflammatory bowel disease: standardized classification with provisional clinical implications*, Hum. Pathol., 14:931-968 (1983).

While cancer screening is very important for early detection and treatment, many biologic processes exist that cannot be easily or directly monitored with visible microscopy. Additionally, these processes also cannot be easily or directly monitored using advanced analysis/imaging tools such as magnetic resonance imaging (MRI), computer tomography (CT), or nuclear imaging, due to the fact that key molecules in these processes are not distinguishable from each other via these methodologies. Due to these factors, direct visual observation, both externally and endoscopically, is generally used, including colorectal screening, gastric and dermatological applications. However, while the human eye can process many visual cues, several of the early molecular changes associated with cancer are simply not discernable by even the most skilled practitioners. For example, routine endoscopy for colorectal cancer screening has a miss rate of up to 24%, with substantially higher figures when the lesions are flat. D. K. Rex et al., *Colonoscopic miss rates of adenomas determined by back-to-back colonoscopies*. Gastroenterology, 112:24-28 (1997); B. J. Rembacken et al. *Flat and depressed colonic neoplasms: a prospective study of 1000 colonoscopies in the UK*, Lancet, 355:1211-1214 (2000).

In response to these shortcomings, several other techniques have been developed for cancer and precancerous evaluation. D. Benaron, D. Stevenson, *Optical time-of-flight and absorbance imaging of biologic media*, Science, 259:1463-1466 (1993); B. Chance, *Near-infrared images using continuous, phase-modulated, and pulse light with quantitation of blood and blood oxygenation*. Ann. NY Acad. Sci., 838:29-45 (1993); R. Alfano et al., *Advances in optical imaging of biomedical media*, Ann. NY Acad. Sci., 820:248-270 (1997); S. Andersson-Engels et al., *In vivo fluorescence imaging for tissue diagnostics*, Phys. Med. Biol., 42:815-824 (1997); P. Contag et al., *Bioluminescent indicators in living mammals*, Nature Med., 4:245-247 (1998); J. C. Hebden, D. T. Delpy, *Diagnostic imaging with light*, Br. J. Radiol., 70:S206-S214 (1997); R. Manoharan et al., *Raman spectroscopy and fluorescence photon migration for breast cancer diagnosis and imaging*, Photochem. Photobiol., 67:15-22 (1998); G. Tearny et al., *In vivo endoscopic optical biopsy with optical coherence tomography*, Science, 276:2037-2039 (1997).

Fluorescence-based cancer imaging and detection makes use of the fluorescence characteristics of naturally occurring molecules such as collagen, nicotinamide adenine dinucleotide, flavins, and porphyrins, that is, the study of natural fluorescent compounds. Such systems are said to be characterized by auto-fluorescence. In contrast, the addition of compounds to the tissue or cellular system (i.e., exogenous fluorophores) may be performed with a goal of preferential accumulation in the neoplastic tissue. C. Arens et al., *Indirect fluorescence laryngoscopy in the diagnosis of precancerous and cancerous laryngeal lesions*, Eur. Arch. Otorhinolaryngol, 264:621-626 (2007). It is known that malignant tumors can accumulate endogenous fluorophores (i.e., auto-fluorescence). A. Policard, *Etude sur les aspects offerts par des tumours experimentales examinees a la lumiere de Wood*, CR Soc. Biol., 91:742-743 (1924). Additionally, benign and malignant tumors may have differences that can be detected by fluorescence techniques. R. Alfano et al., *Laser induced fluorescence spectroscopy from native cancerous and normal tissue*, IEEE J. Quantum Electron, 20:284-291 (1984).

Fluorescence spectroscopy has been used to attempt to diagnose cervical intraepithelial neoplasia (CIN), an important dysplastic precancerous change in which histological changes are confined to the epithelial layer. A. Mahadevan et al., *Study of the fluorescence properties of normal and neoplastic human cervical tissue*, Lasers Surg. Med., 13:647-655 (1993). In addition, endoscopic detection of gastrointestinal cancers and diseases is an excellent example of a clinical application of fluorescence spectroscopy for real-time, non-invasive detection of dysplasia and early cancer. C. Arens et al., *Indirect fluorescence laryngoscopy in the diagnosis of precancerous and cancerous laryngeal lesions*, supra.Eur. Arch. Otorhinolaryngol, 264:621-626 (2007); J. Haringsma, G. N. J. Tytgat, *Fluorescence and autofluorescence*, Bailliere's Clinical Gastroenterology, 13:1-10 (1999). Other important applications for auto-fluorescence techniques include colorectal cancer screening, oral oncology, and in vivo imaging of enzyme activity. D. P. Hurlstone, S. Brown, *Techniques for targeting screening in ulcerative colitis*, Postgrad. Med. J., 83:451-460 (2007); B. W. Chwirot et al., *Spectrally resolved fluorescence imaging of human colonic adenomas*, J. Photochem. Photobiol. B: Biol., 50:174-183 (1999); D. C. G. De Veld et al., *The status of in vivo autofluorescence spectroscopy and imaging for oral oncology*, Oral Oncology, 41:117-131 (2005); M. A. Funovics et al., *Catheter-based in vivo imaging of enzyme activity and gene expression: feasibility study in mice*, Radiology, 231:659-666 (2004).

In addition to fluorescence as described above, other optical techniques include Raman spectroscopy and multi-photon fluorescence. Raman spectroscopy is a inelastic light scattering process in which incident photons either add (Stokes shift) or subtract (Anti-Stokes shift) energy to the vibrational energy of the host material, resulting in an energy shift of the subsequently scattered photon. Because Raman scattering (i.e., Raman spectroscopy) is sensitive to the local molecular structure, it has been used as an optical sensing technique, including for cancer detection. K. Sokolov et al., Optical systems for in vivo molecular imaging of cancer, Tech. in Cancer Res. & Treatment, 2:491-504 (2003); U. Utzinger et al., *Near-infrared Raman spectroscopy for in vivo detection of cervical percancers*, Appl. Spectroscopy, 55:955-959 (2001). Multi-photon fluorescence uses a combination of two or more photons to excite the target molecular structure, after which typical fluorescence processes, as discussed above, occur. By using multiple photons of longer wavelength, better imaging (notably biological imaging) can be obtained by eliminating problems such as matrix attenuation of light related to, for example, shorter wavelength, single-photon fluorescence, out-of-plane fluorescence, and/or photobleaching. D. J. Stephens, et al., *Light microscopy techniques for live cell imaging*, Science, 300:82-86 (2003).

Clinical applicability of fluorescence, and other optical techniques described above, has been limited by large patient-to-patient variations in fluorescence properties, as well as non-uniform uptake and distribution of exogenous fluorescence agents and biomarkers. C. Arens et al., Indirect fluorescence laryngoscopy in the diagnosis of precancerous and cancerous laryngeal lesions, supra.Eur. Arch. Otorhinolaryngol., 264:621-626 (2007); S.F. Martin et al., Fluorescence spectroscopy of an in vitro model of human cervical precancer identifies neoplastic phenotype, Int. J. Cancer, 120: 1964-1970 (2007); C. Brookner et al., Effects of biographical variables on cervical fluorescence emission spectra, J. Biomed. Optics., 8:479-483 (2003). While fluorescence and Raman techniques have been a valuable source of diagnostic information for detecting precancerous tumors, many drawbacks still exist in the art. The development of improved methods for cancer screening could help increase the percentage of early detection and curable cancer cases. Similarly, the addition of further functionality to biological imaging schemes (e.g., fluorescence and multi-photon) is also desirable.

BRIEF SUMMARY

Embodiments of the present invention provide a method and apparatus for imaging or sensing a material. In one embodiment, a first image or signal (e.g., fluorescent or Raman spectroscopy) of a material can be recorded, the material can then be perturbed, and then a second image or signal (e.g., fluorescent or Raman spectroscopy) of the material can be recorded. The two images or signals can be subtracted to give a differential image or signal. In a specific embodiment, the first image or signal and the second image or signal can be fluorescent images. In further embodiments, the first and second images or signals can be other optical images or signals, such as Raman spectroscopy images or signals. The optical signals can be, for example, a spectrum, a single channel photo multiplier tube signal, and/or a signal at a single wavelength or two or more wavelengths.

In an embodiment, a method in accordance with the present invention involves exciting a material with radiation having a first wavelength; recording a first fluorescent image or signal from the material; perturbing the material with radiation having a second wavelength; exciting the material with radiation having the first wavelength; recording a second fluorescent image or signal from the material; and subtracting the first fluorescent image or signal from the second fluorescent image or signal to give a differential fluorescent image or signal. In yet a further embodiment, the material can be perturbed by a multi-photon process, such as a series of femtosecond or other ultrashort laser pulses. The femtosecond laser pulses can each be at the same wavelength, or a combination of wavelengths.

In embodiments where a material is perturbed with irradiation from a laser, the laser can have a wavelength in the ultraviolet (UV) range. For example, the laser can have a wavelength of about 193 nm or about 213 nm. In a specific embodiment, the material can be perturbed with irradiation from an ArF laser at a wavelength of about 193 nm. In an alternative embodiment, the material can be perturbed with irradiation from a quintupled Nd:YAG laser at a wavelength of about 213 nm. In other alternative embodiments, the material can be perturbed with a KrF laser at the wavelength of about 248 nm, or with radiation from a tunable light source such as an OPO laser or a Ti:Sapphire laser in which the laser output is tuned to a specific wavelength or wavelength region to optimize the perturbation process for a specific material or targeted feature. In a specific embodiment, the perturbation can involve targeting labeled or artificial chromophores, such as fluorescent tags.

DETAILED DISCLOSURE

Figure 1A:
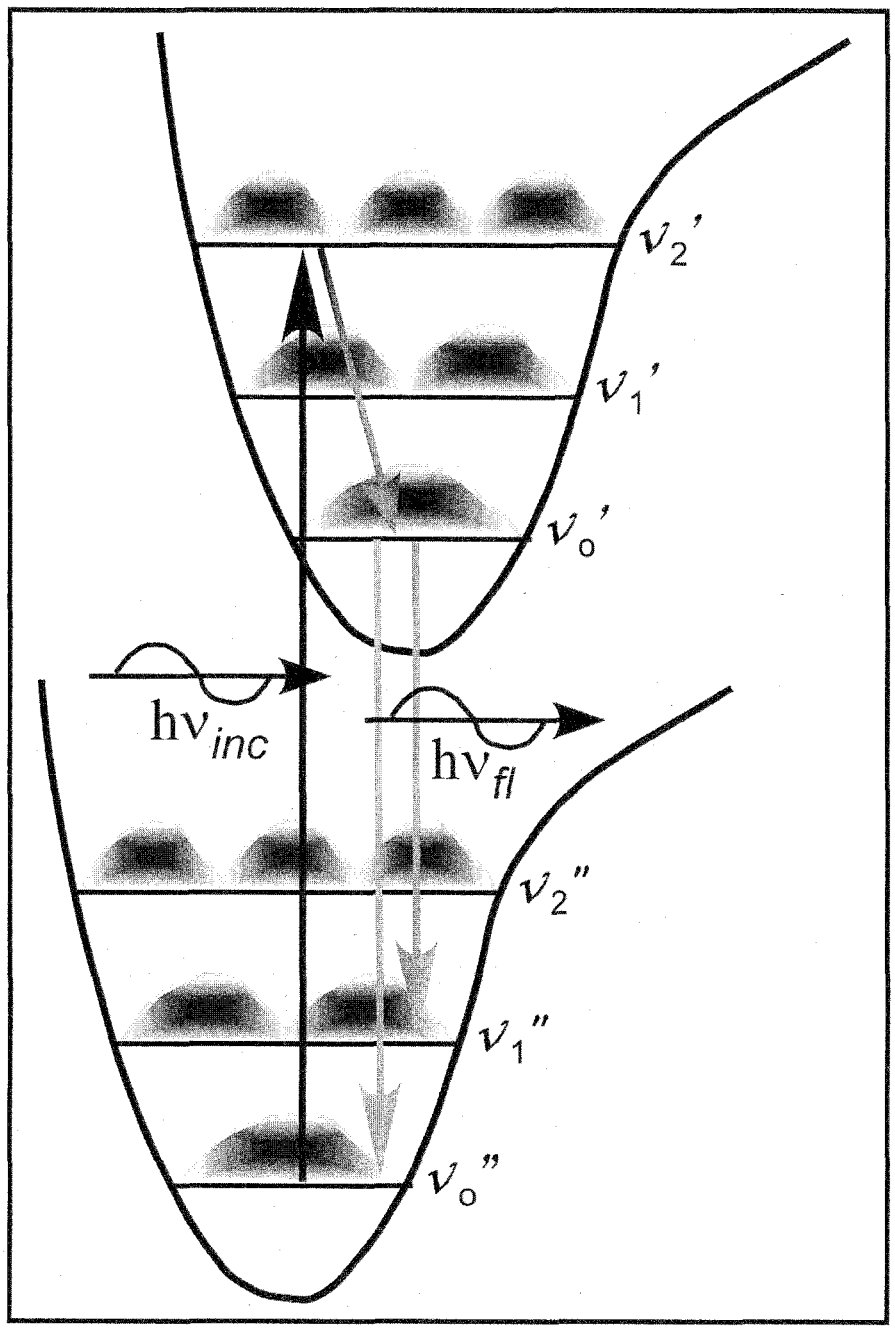
FIG. 1A shows an absorption and relaxation of a fluorescent process.

Embodiments of the present invention provide a method and apparatus for Differential Laser-Induced Perturbation (DLIP). Specific embodiments can be referred to as Differential Laser-Induced Fluorescence (DLIF), where the sensing metric is via a fluorescence process. Fluorescence techniques, or other suitable optical techniques such as Raman spectroscopy, can be combined with the use of a perturbing laser pulse. The perturbing laser pulse can disrupt the targeted optical response (e.g., fluorescence or Raman scattering) of the material, thereby altering the fluorescence or Raman scattering image or signal.

According to embodiments of the present invention, a first fluorescent image or signal of a material can be recorded, the material can then be perturbed with one or more laser pulses, and then a second fluorescent image or signal of the material can be recorded. The two fluorescent images or optical signals can be subtracted one from the other to give a differential image or optical signal. Because the perturbation is related to the material properties, the differential fluorescent image or optical signal can reveal information unavailable with normal fluorescence or optical techniques.

In an embodiment, a method of the present invention involves exciting a material with radiation having a first wavelength; recording a first fluorescent image or signal from the material; perturbing the material with radiation having a second wavelength; exciting the material with radiation having the first wavelength; recording a second fluorescent image or signal from the material; and subtracting the first fluorescent image or signal from the second fluorescent image or signal to give a differential fluorescent image or signal. In a further embodiment, the material can be perturbed by a multi-photon process, for example, a series of femtosecond or other ultrashort laser pulses. The femtosecond laser pulses can each be at the same wavelength or a combination of wavelengths.

Specific embodiments can involve perturbing the material, after recording a first image or signal, with radiation having the same wavelength as the radiation used to excite the material for recording the first image or signal. In a specific embodiment, the material can be perturbed with radiation having the same wavelength as the excitation radiation, but with a greater intensity. The radiation for the perturbation can be produced by, for example, a diode or flashlamp.

In embodiments where a material is perturbed with irradiation from a laser, the laser can have a wavelength in the ultraviolet (UV) range. In an embodiment, the laser can have a wavelength of from about 10 nm to about 400 nm. In a further embodiment, the laser can have a wavelength of from about 100 nm to about 400 nm. In yet a further embodiment, the laser can have a wavelength of from about 100 nm to about 280 nm. In yet a further embodiment, the laser can have a wavelength of from about 150 nm to about 250 nm. In yet a further embodiment, the laser can have a wavelength of from about 175 nm to about 225 nm. In yet a further embodiment, the laser can have a wavelength of from about 193 nm to about 213 nm. In yet a further embodiment, the laser can have a wavelength of about 193 nm. In yet a further embodiment, the laser can have a wavelength of about 213 nm.

In a specific embodiment, the material can be perturbed with irradiation from an ArF laser at a wavelength of about 193 nm. In an alternative embodiment, the material can be perturbed with irradiation from a quintupled Nd:YAG laser at a wavelength of about 213 nm. In other alternative embodiments, the material can be perturbed with a KrF laser at the wavelength of about 248 nm, or with radiation from a tunable light source such as an OPO laser or a Ti:Sapphire laser in which the laser output is tuned to a specific wavelength or wavelength region to optimize the perturbation process for a specific material or targeted feature.

In one embodiment, the first wavelength for exciting the material can be from about 10 nm to about 400 nm. In a further embodiment, the first wavelength for exciting the material can be from about 100 nm to about 400 nm. In yet a further embodiment, the first wavelength for exciting the material can be from about 200 nm to about 400 nm. In yet a further embodiment, the first wavelength for exciting the material can be from about 300 nm to about 400 nm. In yet a further embodiment, the first wavelength for exciting the material can be about 355 nm.

Methods of the present invention are not limited to a fluorescent probe. In an embodiment, Raman spectroscopy can be used as a differential probe. In a further embodiment, fluorescence lifetime, which probes time-dependence of a fluorescence signal, can be used as a differential probe. In a further embodiment, a multi-photon fluorescence signal can be used as a differential probe. In a further embodiment, a Raman scattering probe can be used as a differential probe. In a further embodiment, a photofragmentation signal can be used as a differential probe. In a further embodiment, a light scattering or reflectivity signal can be used as a differential probe. In a further embodiment, combinations of the above (i.e., fluorescence, fluorescence lifetime, multi-photon fluorescence, Raman scattering, photofragmentation and/or light scattering or reflectivity) can be used as a differential probe.

Methods of the present invention provide improved specificity in detecting material properties. The detection and analysis of fluorescent light can provide discrimination among emitting materials because the excitation/emission wavelength pair are a combination of both the molecular structure and the overall molecular and material environment (e.g., the tissue matrix and/or chemical sample).

Embodiments of the present invention take advantage of interactions of excitation radiation, such as incident photons and perturbing photons, with material properties. The mechanisms of photon coupling to particular molecular bonds, which include induced photochemistry, bond cleaving, the role of internal relaxation processes, and/or the subsequent fluorescent radiative decay, can lead to accurate sensitivity and selectivity of material properties.

In certain embodiments, methods of the present invention can be used to detect material properties of biological tissues. Descriptions and models of the interaction between visible and ultraviolet radiation, for example, laser radiation, and biological tissue can be formulated in terms of the Beer-Lambert law, as described in Equation (1).

$$I(x) = I_0 \exp(-\alpha x). \tag{1}$$

In Equation 1, I(x) is the radiation intensity after penetrating to depth x (cm) in a biological tissue, $I_0$ is the light intensity incident on the biological tissue surface (x=0), and $\alpha$ ($cm^{-1}$) is the tissue absorption coefficient for the wavelength of interest. For example, corneal tissue has a static tissue absorption coefficient of about 16,000 $cm^{-1}$ at a wavelength of about 193 nm, based on direct measurement of the absorption cross-sections of peptide bonds and amino acids characteristic of corneal collagen, and the overall composition of corneal tissue. B. T. Fisher and D. W. Hahn, *Measurement of Small-Signal Absorption Coefficient and Absorption Cross-Section of Collagen for* 193-*nm Excimer Laser Light and the Role of Collagen in Tissue Ablation*, Applied Optics., 43:5443-5451 (2004).

While the formulation of the Beer-Lambert law is straightforward, it in actuality can be considered a first-order approximation based on an average and static value of the absorption coefficient. When dealing with pulsed laser irradiation of a wavelength in the ultraviolet (UV) range, or with intense photon fluxes from ultrafast laser pulses (e.g., femtosecond pulses), the interaction of photons and chromophores can be a dynamic process during which the absorption coefficient can change as electronic states are altered via absorption, and chemical bonds in the biomolecular matrix can be altered in real-time. For example, with 193-nm excitation, such as that from an ArF excimer laser, the photon energy is about 6.4 eV, which exceeds the bond energy of many molecular structures since C—C and C—O bonds have bond energies of about 3.6 eV, and C=C bonds have a bond energy less than about 6.4 eV. Bond breakage in biological tissues can lead to intermediate product formation. B. T. Fisher and D. W. Hahn, *Development and Numerical Solution of a Mechanistic Model for Corneal Tissue Ablation with the* 193-*nm Argon Fluoride Excimer Laser*, J. Optical Society of America B: Optics, Image Science & Vision, 24:265-277 (2007).

A biological matrix can be altered by radiation, and the fluorescent properties of the biological matrix can be perturbed. In an embodiment of the present invention, the radiation can be low intensity or sub-ablative radiation. In a further embodiment, the radiation can be UV radiation. In yet a further embodiment, the radiation can be UV radiation with a wavelength of from about 150 nm to about 250 nm. In yet a further embodiment, the radiation can be UV radiation with a wavelength of from about 175 nm to about 225 nm. In yet a further embodiment, the radiation can be UV radiation with a wavelength of from about 193 nm to about 213 nm. In yet a further embodiment, the radiation can be UV radiation with a wavelength of about 193 nm. In other alternative embodiments, the material can be perturbed with a KrF laser at the wavelength of about 248 nm, or with radiation from a tunable light source such as an OPO laser or a Ti:Sapphire laser in which the laser output is tuned to a specific wavelength or wavelength region to optimize the perturbation process for a specific material or targeted feature.

Figure 1B:
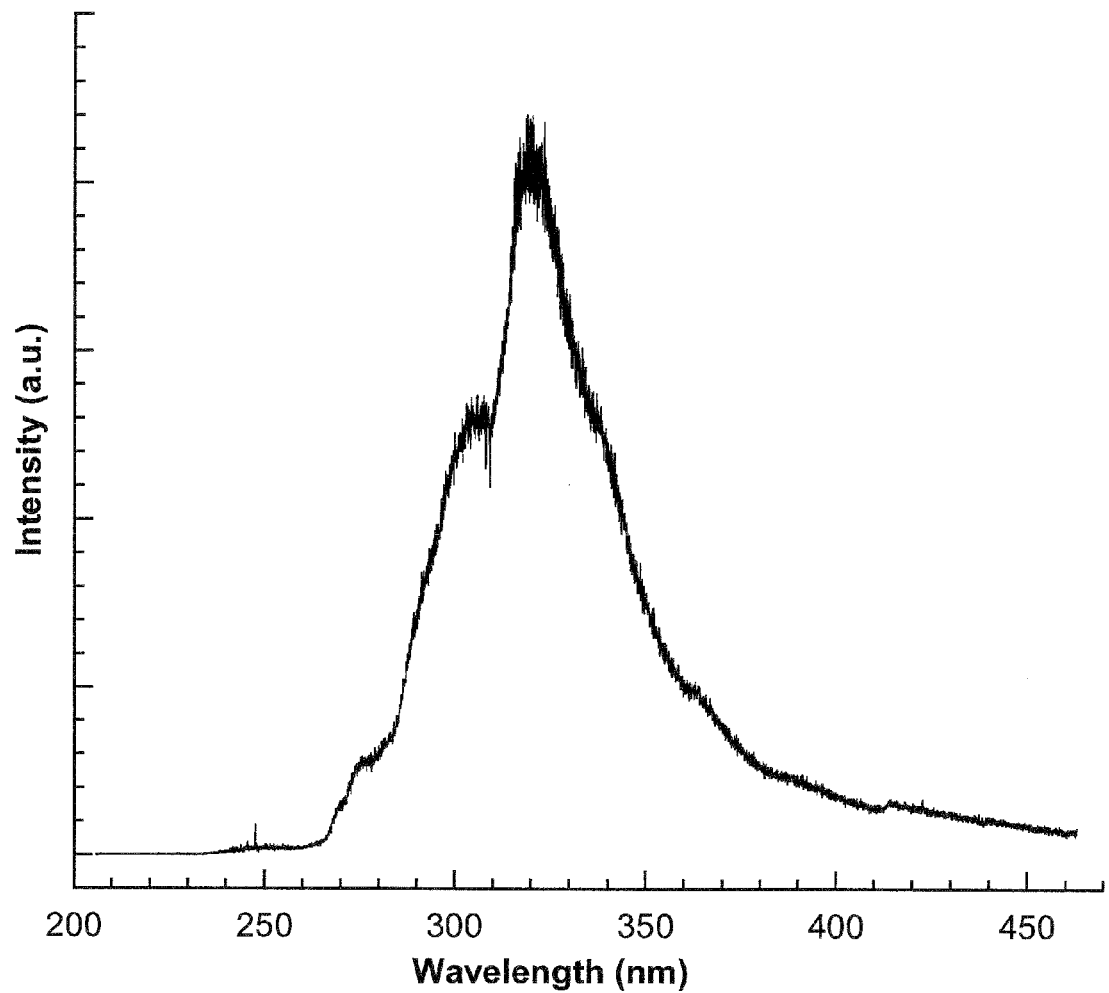
FIG. 1B shows fluorescence emission from bovine corneal tissue following perturbation with radiation at a wavelength of about 193 nm.

FIG. 1B shows a fluorescence emission spectrum from bovine corneal tissue following perturbation with radiation at a wavelength of about 193 nm.

Probing biological tissue or other targeted materials (e.g., hazardous chemicals) with fluorescent monitoring, such as auto-fluorescence or pharmacologically induced fluorescence (PIF), before and after perturbation can provide a differential response in a fluorescence image. For example, because of the intimate coupling of the perturbing source to the biological matrix, molecular structures of abnormal tissue, such as dysplastic precancerous regions, can manifest differently than normal tissue structure. The differential laser-induced perturbation (DLIP) and differential laser-induced fluorescence (DLIF) methods of the present invention examine differences in fluorescence images (or other optical sensing scheme such as Raman scattering), so many variations in the absolute fluorescence or optical sensing properties as generally observed in patient-to-patient populations can be mitigated. When performed on biological tissue, the DLIP techniques of the subject invention take advantage of the specificity of laser-tissue coupling with difference spectroscopy to form sensitive biodetection and/or bioimaging scheme.

Figure 2:
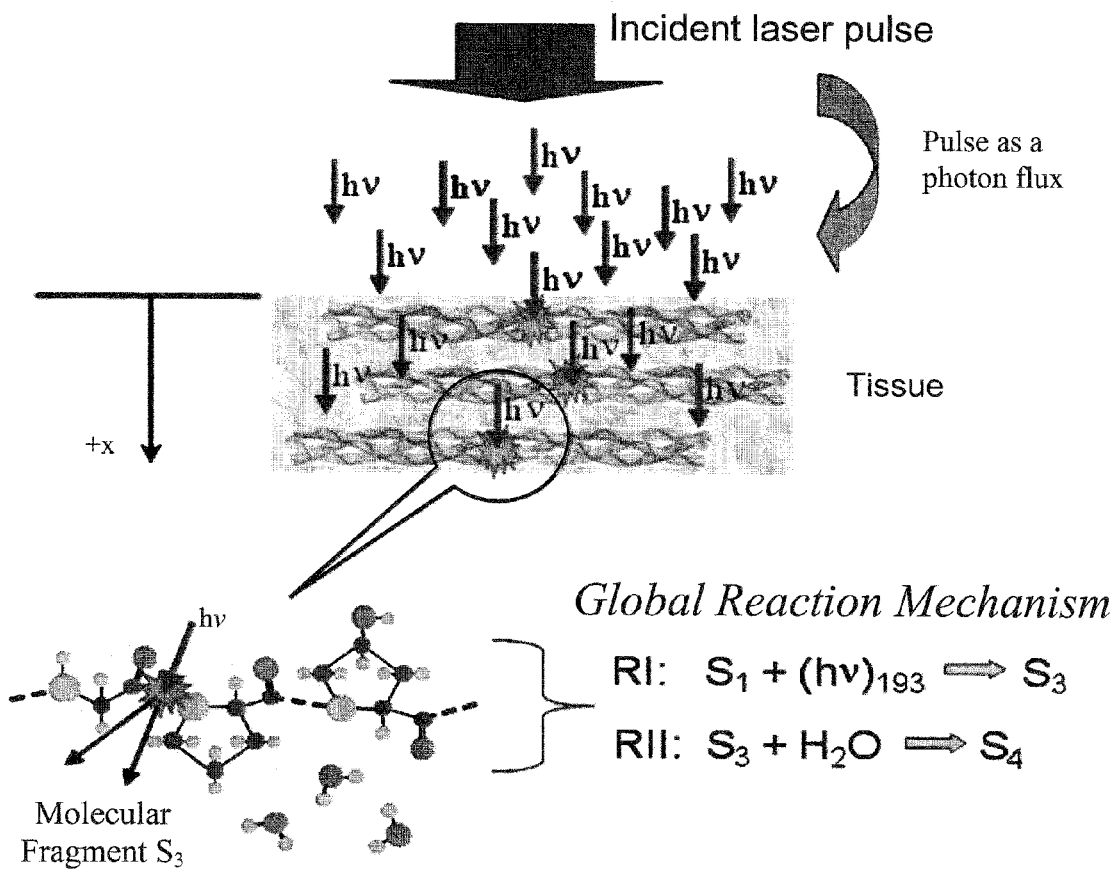
FIG. 2 shows a photochemical interaction of light with a biological tissue matrix.

In an embodiment, the DLIF techniques of the present invention can be performed on biological tissue with a deep UV laser used for perturbing the tissue. Deep UV laser irradiation (with photon energy of at least about 6 eV) can be strongly absorbed by biological tissues and can photochemically cleave molecular bonds within a cellular matrix. In a specific embodiment, photon energy of 6 eV or greater is used. FIG. 2 illustrates the photochemical interaction of light with a biological tissue matrix.

The combination of probing, perturbation and repeat probing can add a new spectral dimension strongly coupled to the tested material, thereby providing enhanced sensitivity and specificity. In addition, when performed on biological tissue, the DILF techniques according to embodiments of the present invention can help mitigate patient-to-patient variation.

Embodiments of the present invention can be used to provide improved detection methods in a wide variety of areas. For example, cancer detection and screening, both in vivo and in a pathology laboratory, and fluorescence microscopy can each benefit from the exceptional sensitivity and specificity of the methods of the present invention (i.e., information power or orthogonal sensing) over traditional fluorescence. By perturbing the tested material and taking a differential image, a high level of specificity can be realized. Other embodiments may be used for determination or identification of biological contaminants (e.g., *Escherichia coli* or *Staphylococcus*), or determination of biological weapons (e.g., *Bacillus anthracis*), or chemical munitions, both remotely or locally, (e.g., explosive compounds such as TNT or RDX).

Aspects of the invention, such as subtraction of one image or signal from another image or signal, can be accomplished via many techniques known in the art and may be described in the general context of computer-executable instructions, such as program modules, being executed by a computer. In specific embodiments, subtraction of one image or signal from another image or signal, as well as other elements of the invention, can be performed using a computer program module, which can include software, hardware, firmware, circuits, and/or computer programs. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Specific hardware devices, programming languages, components, processes, protocols, and numerous details including operating environments and the like can be used with embodiments of the present invention. In certain instances, structures, devices, and processes are described by the function performed, rather than in detail, to avoid obscuring the present invention. But an ordinary-skilled artisan would understand that the present invention may be practiced without these specific details. Computer systems, servers, work stations, and other machines may be connected to one another across a communication medium including, for example, a network or networks.

As one skilled in the art will appreciate, embodiments of the present invention may be embodied as, among other things: a method, system, or computer-program product. Accordingly, the embodiments may take the form of a hardware embodiment, a software embodiment, or an embodiment combining software and hardware. In an embodiment, the present invention takes the form of a computer-program product that includes computer-useable instructions embodied on one or more computer-readable media.

Computer-readable media include both volatile and non-volatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The present invention may be practiced in a network environment such as a communications network. Such networks are widely used to connect various types of network elements, such as routers, servers, gateways, and so forth. Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the present invention is not limited by the forms and communication protocols described herein.

Exemplary Embodiments

The following exemplary embodiments are provided for illustration and are not intended to be limiting.

Embodiment 1. A method for imaging or sensing a material, comprising:
exciting a material with radiation having a first wavelength;
recording a first image or signal from the material;
perturbing the material;
exciting the material with radiation having the first wavelength;
recording a second image or signal from the material; and
subtracting the first image or signal from the second image or signal to give a differential image or signal.

Embodiment 2. The method according to embodiment 1, wherein the first image or signal is a first fluorescent image and the second image or signal is a second fluorescent image.

Embodiment 3. The method according to embodiment 1, wherein the first image or signal is a first optical signal and the second image or signal is a second optical signal.

Embodiment 4. The method according to embodiment 1, wherein perturbing the material comprises perturbing the material with irradiation from a laser at a second wavelength.

Embodiment 5. The method according to any of embodiments 1-4, wherein the irradiation is ultraviolet (UV) irradiation.

Embodiment 6. The method according to any of embodiments 4-5, wherein the second wavelength is from about 150 nm to about 250 nm.

Embodiment 7. The method according to any of embodiments 4-5, wherein the second wavelength is from about 193 nm to about 213 nm.

Embodiment 86. The method according to any of embodiments 4-5, wherein the second wavelength is about 193 nm.

Embodiment 9. The method according to any of embodiments 4-5, wherein the second wavelength is about 213 nm.

Embodiment 10. The method according to embodiment 4, wherein the second wavelength is about 248 nm.

Embodiment 11. The method according to embodiment 4, wherein the laser is a KrF laser.

Embodiment 12. The method according to embodiment 4, wherein the laser is a tunable OPO laser.

Embodiment 13. The method according to embodiment 4, wherein the laser is tunable Ti:Sapphire laser.

Embodiment 14. The method according to embodiment 4, wherein perturbing the material comprises perturbing the material with irradiation from a light source at a second wavelength.

Embodiment 15. The method according to any of embodiments 1-14, wherein the first wavelength is about 355 nm.

Embodiment 16. The method according to embodiment 4, wherein the laser is an ArF excimer laser.

Embodiment 17. The method according to embodiment 4, wherein the radiation having a first wavelength is produced by a quintupled Nd:YAG laser.

Embodiment 18. The method according to any of embodiments 1-17, wherein perturbing the material comprises perturbing the material with a multi-photon process.

Embodiment 19. The method according to embodiment 18, wherein the multi-photon process comprises subjecting the material to irradiation from a series of pulses from a femtosecond laser or other ultrashort laser pulses.

Embodiment 20. The method according to any of embodiments 1-19, wherein the material comprises a biological tissue and/or chemical sample.

Embodiment 21. The method according to embodiment 4, wherein the second wavelength is the same as the first wavelength.

EXAMPLES

For all examples, the fluorescent imaging was performed using the output of a tripled Nd:YAG laser operating at a wavelength of 355 nm, with a pulse width of 8 ns, and a pulse energy between 50 µJ/pulse and 1 mJ/pulse. The laser beam was expanded to a beam diameter of approximately 1 cm. The 355-nm laser was directly downward toward the horizontal sample plane at an angle of incidence of about 60 degrees to the surface normal. A UV-grade achromatic lens was used to image the target surface onto an intensified CCD (ICCD) array detector with near unity magnification. An additional sharp-edge filter was used to reject with $10^6$ opacity any 355-nm radiation reflected from the target surface. The Q-switch of the laser was used to trigger the ICCD and a 400-ns detection gate was then used to record the image. An ArF excimer laser operating at a wavelength of 193 nm was used for the perturbation laser. The laser was able to deliver a grid of points, each with a nominally 1-mm diameter beam, by scanning over the surface at a fixed laser repetition rate of 60 Hz. The 1-mm ArF beam diameter was approximately Gaussian. The pulse width of the ArF laser was about 9 ns, and the pulse energy was varied between 50 and 250 µJ/pulse. The laser fluence of both the 355-nm fluorescent excitation laser and the 193-nm activation laser were well below the typical thresholds for material ablation. It is noted that all results were stable with time, hence these perturbations were to the material matrix and not some temporary photobleaching effect.

For all examples, the overall procedure was: (1) The target was secured at the fixed imaging plane, and a fluorescent image was recorded using an average of 25 laser shots for the 355-nm excitation laser, (2) the sample was treated with an array of laser shots from the 193-nm excimer laser, and (3) a second fluorescent image was recorded using an average of 25 laser shots for the 355-nm excitation laser. The final DLIF image was taken to be the difference of the final fluorescent image and the initial fluorescent image.

Example 1

U.S. Currency

Figure 3A:
FIGS. 3A and 3B show a white light visible image and a 355-nm fluorescent image of the seal of a U.S. $5 bill, respectively.
Figure 3B:
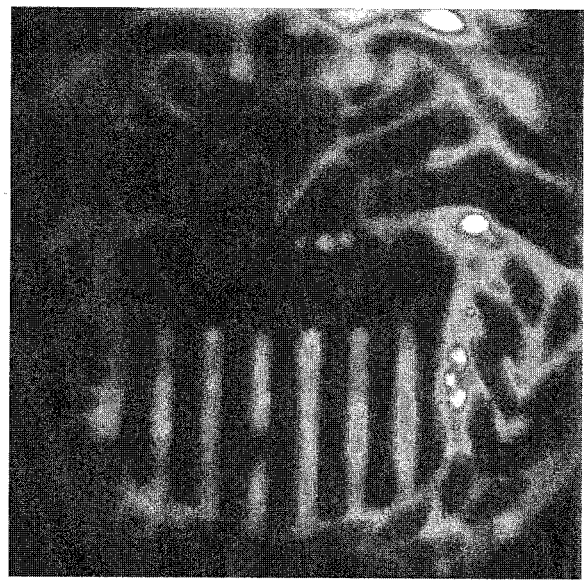

FIG. 3A shows a white light visible image of the seal of a U.S. \$5 bill, and FIG. 3B shows a 355-nm fluorescent image of the seal of the bill. Both images have similar false-color intensity scales, and the full frame is approximately equal to 1 cm. Both images were recorded with the ICCD system. The white light visible image is a simple visual image recorded with a broadband white light illumination source and a wide detection gate (500 µs), and the fluorescent image was recorded using the 355-nm excitation laser.

Example 2

White Card Stock

Figure 4A:
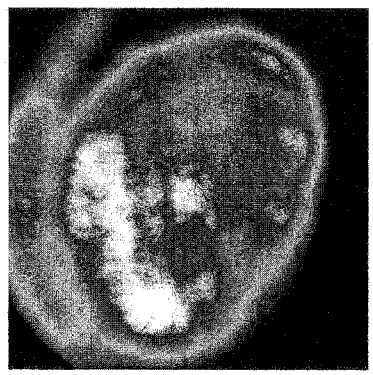
FIGS. 4A-4C show a pre-treatment fluorescent image of white card stock, a post-treatment fluorescence image, and a Differential Laser-Induced Fluorescence (DLIF) image, respectively.
Figure 4B:
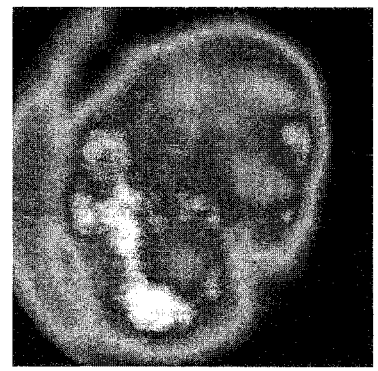
Figure 4C:
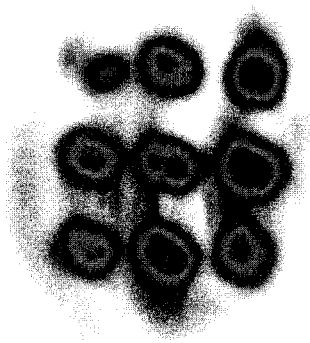

White card stock (standard business card) was used to provide an organic matrix characterized by significant endogenous fluorescence. In this example, the 355-nm fluorescent excitation laser energy was set to about 1 mJ/pulse, and the 193-nm treatment laser was set to about 100 µJ/pulse. For 193-nm perturbation, a 3×3 grid was applied with each point on the grid receiving 100 excimer laser shots. FIG. 4A shows the pre-treatment fluorescent image, FIG. 4B shows the post-treatment fluorescence image, and FIG. 4C shows the DLIF image. The full frame for each image is approximately equal to 1 cm. Though the overall beam homogeneity of the 355-nm excitation beam was not high quality, the difference spectrum revealed excellent sensitivity to the induced photochemical perturbations to the fluorescence. The excimer laser treatment reduced the fluorescence intensity of the treated spots.

Example 3

Collagen Films

Figure 5A:
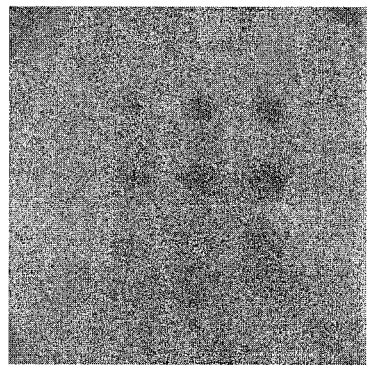
FIGS. 5A-5C show DLIF images for thin collagen film exposed to 20 shots, 60 shots and 120 shots, respectively, of a 100 μJ/pulse excimer laser delivered to each point in the grid.
Figure 5B:
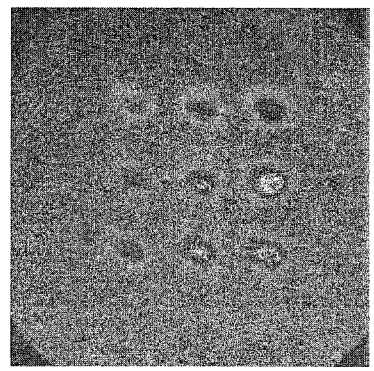
Figure 5C:
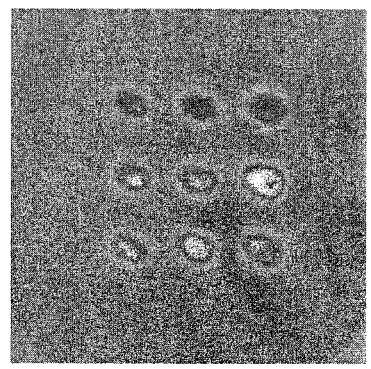

Collagen films were used to provide an organic matrix representative of skin and other tissue matrices. For preparation, type III calfskin collagen was dissolved in 0.5 N acetic acid to create a solution with concentration of 1 mg/mL. The collagen solution was completely dissolved, and approximately 5 mL of solution was deposited on a 50-mm diameter quartz flat and allowed to dry for 48 hours. The average film thickness, as measured by white-light interferometry, was 3.2±0.5 µm (15% RSD). For these experiments, the 355-nm fluorescent excitation laser energy was set to about 50 µJ/pulse, and the 193-nm treatment laser was set to about 100 µJ/pulse. For 193-nm perturbation, a 3×3 grid was applied, with each point on the grid receiving from 20 to 120 excimer laser shots. FIG. 5A shows the DLIF image for 20 193-nm laser shots, FIG. 5B shows the DLIF image for 60 193-nm laser shots, and FIG. 5C shows the DLIF image for 120 193-nm laser shots. For each image, the full frame is approximately equal to 1 cm. The perturbation of the collagen films produced a net increase in fluorescence upon excitation at 355-nm. This suggested that photochemical bond cleavage also reduced fluorescence quenching and fluorescence was enhanced as chromophores were released from the tight collagen matrix and/or the optical properties of the film were modified such that the reflectivity was enhanced. The fluorescent and scattering changes can be decoupled from each other, if desired. In addition, the enhancement scales with the number of laser shots, implying an additive effect. The process was observed to saturate at about 120-150 shots.

Example 4

Amino Acid Films

Figure 6A:
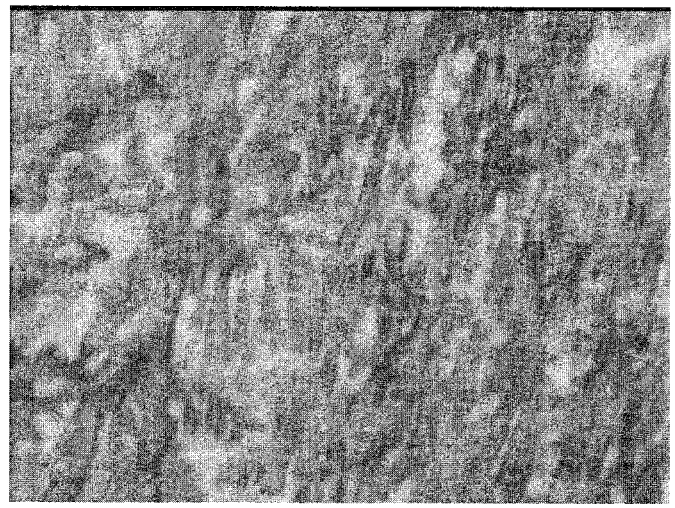
FIGS. 6A-6B show images of an amino acid film taken with optical microscopy before and after excimer laser treatment with 600 193-nm laser shots, respectively.
Figure 6B:
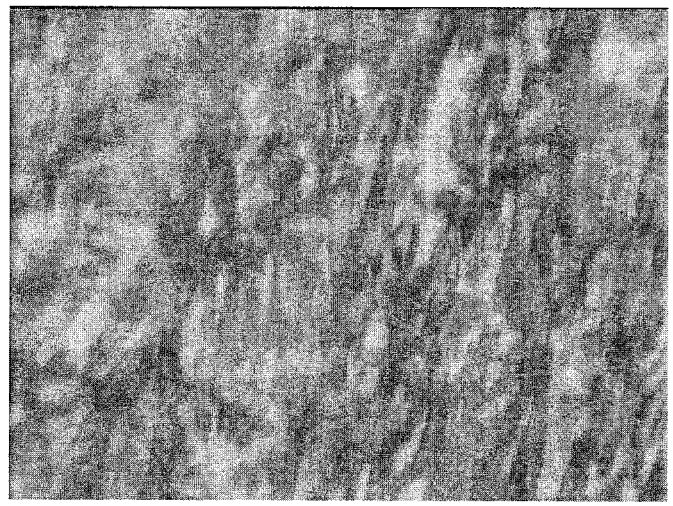
Figure 7A:
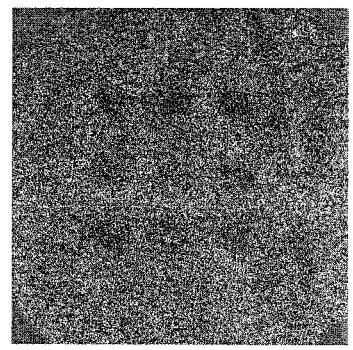
FIGS. 7A-7C show DLIF images for thin amino acid films exposed to 120 shots, 240 shots, and 600 shots, respectively, of a 50 μJ/pulse excimer laser delivered to each point in the grid.
Figure 7B:
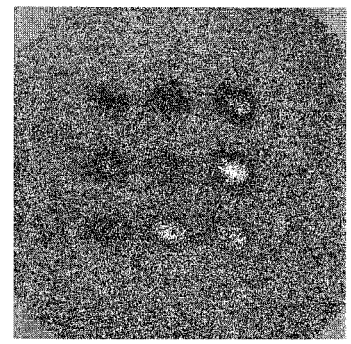
Figure 7C:
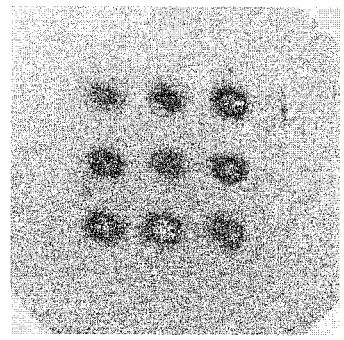

Amino acid films were used to provide an organic matrix representative of skin and other tissue matrices with some peptide bonds missing. These amino acid solutions were created by dissolving appropriate amounts of solid powders of glycine (Sigma Chemical product G7403), L-proline (Fluka product 81709), and cis-4-Hydroxy-L-proline (Fluka product 56248) in 0.5 N acetic acid solution. The ratios were selected to mimic the equivalent concentrations of amino acids in collagen without the peptide bonds. The solution was completely dissolved, and approximately 5 mL of solution was deposited on 50-mm diameter quartz flat and allowed to dry for 48 hours. For this example, the 355-nm fluorescent excitation laser energy was set to about 50 µJ/pulse, and the 193-nm treatment laser was set to about 50 µJ/pulse. For 193-nm perturbation, a 3×3 grid was applied, with each point on the grid receiving from 100 to 600 excimer laser shots. To explore the effects of the 193-nm on the film topography, visible microscopy was used to assess the film surface at the same spot before and after the treatment laser. FIG. 6A shows an optical microscopy image of the amino acid film spot before laser treatment, and FIG. 6B shows an optical microscopy image of the same amino acid film spot after laser treatment with 600 193-nm laser shots. For each image, the full frame is approximately equal to 100 microns. The images in FIGS. 6A and 6B reveal no significant changes in the film structure. FIG. 7A shows the DLIF image for 120 193-nm laser shots, FIG. 7B shows the DLIF image for 240 193-nm laser shots, and FIG. 7C shows the DLIF image for 600 193-nm laser shots. For each image, the full frame is approximately equal to 1 cm. The perturbation of the amino acid films produced a net increase in fluorescence upon excitation at 355-nm, similar to the collagen films. This suggested that photochemical bond cleavage also reduced fluorescence quenching and fluorescence was enhanced as chromophores were released from the tight collagen matrix and/or the optical properties of the film were modified such that the reflectivity was enhanced. The fluorescent and scattering changes can be decoupled from each other, if desired. The dosage was increased to several hundred shots, noting the very low laser fluence for this example of about 50 µJ/pulse.

Example 5

Bovine Eyes

Figure 8A:
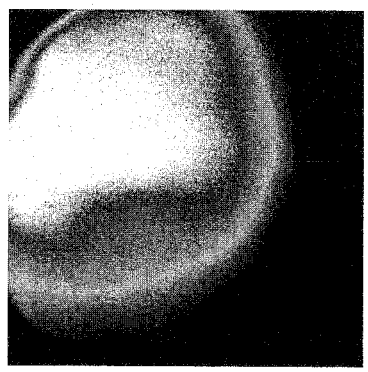
FIGS. 8A-8C show a pre-treatment fluorescent image of a bovine cornea, a post-treatment fluorescence image, and a DLIF image, respectively.
Figure 8B:
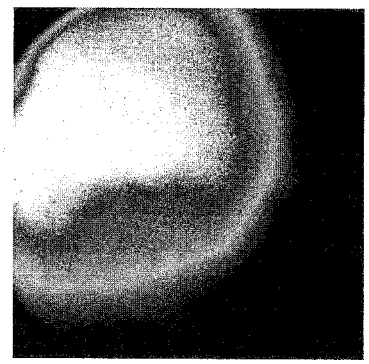
Figure 8C:
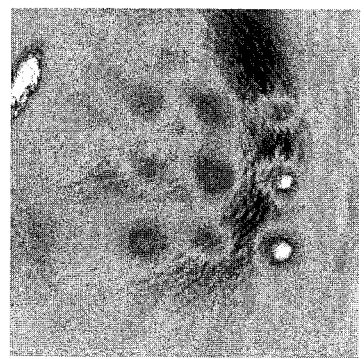

Bovine eyes were used to provide an actual tissue matrix. The experimental conditions are given in: B. T. Fisher and D. W. Hahn, *Development and Numerical Solution of a Mechanistic Model for Corneal Tissue Ablation with the* 193-*nm Argon Fluoride Excimer Laser*, J. Optical Society of America B: Optics, Image Science & Vision, 24:265-277 (2007). For this example, the 355-nm fluorescent excitation laser energy was set to about 100 µJ/pulse, and the 193-nm treatment laser was set to about 130 µJ/pulse. For 193-nm perturbation, a 3×3 grid was applied with each point on the grid receiving 750 excimer laser shots. FIG. 8A shows the pre-treatment fluorescent image of the bovine cornea, FIG. 8B shows the post-treatment fluorescence image of the bovine cornea, and FIG. 8C shows the DLIF image of the bovine cornea. For each image, the full frame is approximately equal to 1 cm. Due to the curvature of the cornea surface, the 355-nm illumination was not uniform and the image plane was somewhat distorted. However, the difference spectrum reveals excellent sensitivity to the induced photochemical perturbations to the fluorescence of actual living tissue. Similar to the collagen films, fluorescence was enhanced with 193-nm perturbation of the collagen matrix. The excimer laser fluence was more than 50 times below the clinical fluence used for typical refractive surgery.

Example 6

Organic Films

Figure 9A:
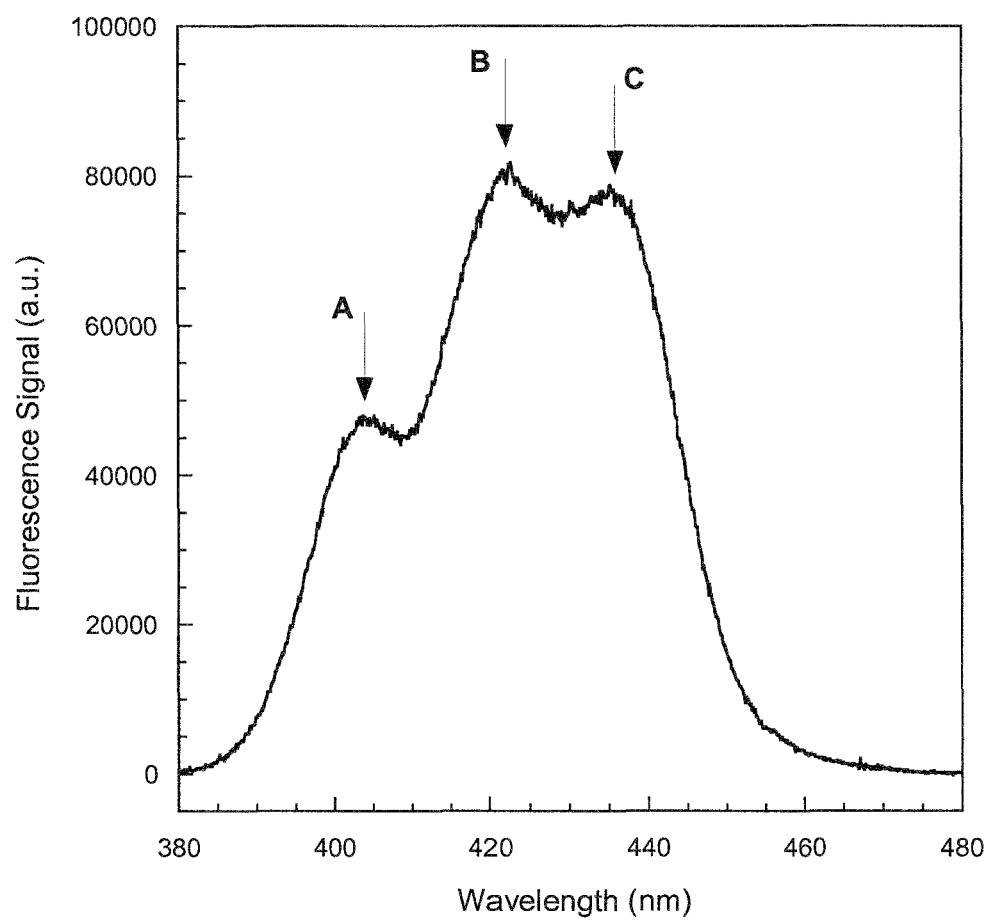
FIG. 9A shows a 355-nm excitation laser fluorescence spectrum of the unperturbed, two-dye mixture (the first spectrum), with spectral bands labeled A, B, and C, where bands A and B correspond to the compound BBQ, and band C corresponds to the compound Coumarin 450.
Figure 9B:
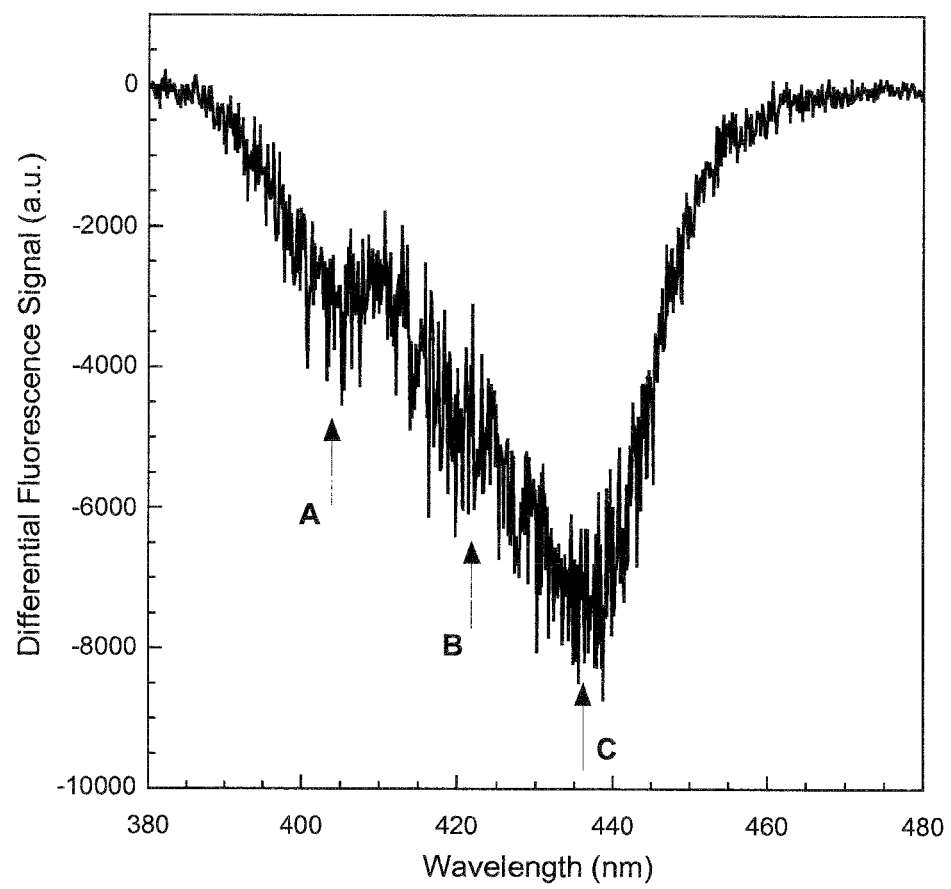
FIG. 9B shows a difference spectrum, with spectral bands labeled A, B, and C, which shows the pre-perturbation spectrum of FIG. 9A (the first spectrum) subtracted from a second spectrum recorded after perturbation of the two-dye mixture with a 193-nm perturbation laser (250 laser pulses at 100 μJ/pulse).
Figure 9C:
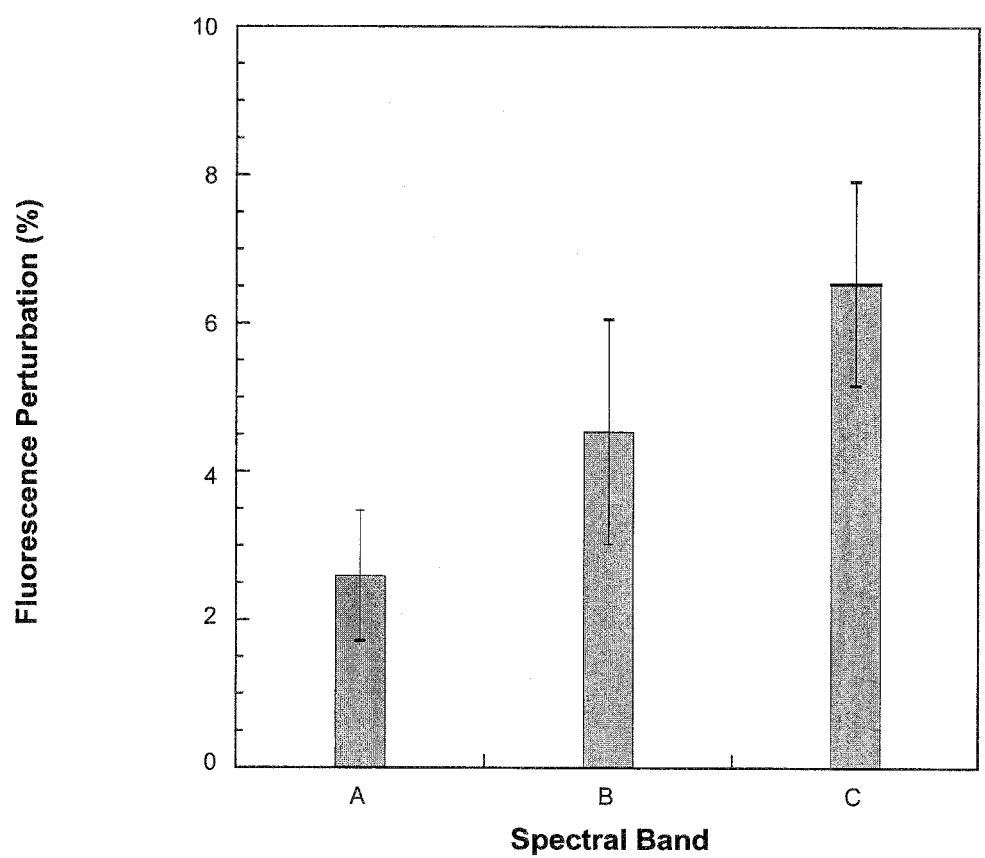
FIG. 9C shows the average perturbation (expressed as the percent decrease) to the fluorescence signal for each of the three spectral bands, A, B, and C.

Thin organic films were used to provide an organic matrix representative of multiple-species, complex systems. These films were created by dissolving 30 mg of Coumarin 450 (CAS no. 26078-25-1) and 30 mg of BBQ (CAS no. 18434-08-7) into 60 ml of reagent grade ethanol. Coumarin 450 ($C_{13}H_{15}NO_2$) is a two-ring structure that contains C—N bonds in addition to a range of C—C, H—C and C—O bonds, while BBQ ($C_{48}H_{66}O_2$) has a four-ring backbone structure and contains a range of C—C, H—C and C—O bonds but no C—N bonds. These two molecules were selected to provide a complex, bi-molecular system. The solution was dissolved for more than 24 hours, and approximately 3 mL of solution was then deposited on a 50-mm diameter quartz flat and allowed to dry for 48 hours. For this example, the 355-nm fluorescence excitation laser energy was set to about 50 µJ/pulse, and the 193-nm perturbation laser energy was set to about 100 µJ/pulse. For the 193-nm perturbation, an approximately 3-mm diameter spot was directly irradiated for a total of 250 shots. To quantify the effects of the 193-nm perturbation, the 355-nm excitation fluorescence was recorded by collecting the fluorescence from an approximately 1.5-mm diameter spot of 355-nm irradiation centered in the middle of the 193-nm treatment spot. Fluorescence emission was collected using a collection lens and fiber-coupled to a 0.3-m spectrometer and then recorded using an intensified CCD array detector synchronized to the 355-nm laser pulse using a 200-ns integration time per pulse. All spectra collected were an ensemble-average of 200 excitation laser pulses. In addition to the spectrometer, a 364-nm sharp edge filter was used to block residual 355-nm light from entering the spectrometer, and a 450-nm low-pass filter was used to remove residual laser light at the wavelength 532 nm. The low-pass filter partially overlapped with the Coumarin 450 fluorescence spectrum. FIG. 9A shows the 355-nm excitation laser fluorescence spectrum of the unperturbed, two-dye mixture, with spectral bands labeled A, B, C; with bands A and B corresponding to the compound BBQ, and the band C corresponding to the compound Coumarin 450, as determined through measurements of the individual compounds. The mixture was then perturbed with the 193-nm as defined above (250 laser pulses at 100 µJ/pulse), and a second fluorescence spectrum was then recorded in the identical manner as the FIG. 9A spectrum. The first spectrum (pre-perturbation) was then subtracted from the second spectrum (post-perturbation) to produce the difference spectrum, which is shown in FIG. 9B. FIG. 9B also shows the same three spectral bands, denoted A, B and C, as depicted in FIG. 9A. Using an approximately 1.7-nm bandwidth about each individual band, the average decrease in fluorescence intensity was then calculated and normalized as a percentage of the original fluorescence intensity of each respective band. This was performed for 10 individual spots, with the results averaged. The average perturbation (expressed as the percent decrease) to the fluorescence signal is presented in FIG. 9C for each of the three spectral bands. The corresponding error bars represent the standard deviation over all 10 measurements. The data reveal a laser-induced perturbation to the fluorescence signals, with a greater perturbation to band C as compared to bands A and B, revealing a selective, differential response of the Coumarin 450 fluorescence signal (band C), as compared to the response of BBQ (bands A and B) to the 193-nm perturbation laser.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method for imaging or sensing a material, comprising:
   irradiating a material with radiation having a first wavelength;
   recording a first image or signal from the material after irradiating the material with the radiation having the first wavelength;
   photochemically perturbing the material after recording the first image or signal from the material;
   irradiating the material with radiation having the first wavelength after photochemically perturbing the material;
   recording a second image or signal from the material after irradiating the material with the radiation having the first wavelength after photochemically perturbing the material; and
   determining, by a computer processor, a difference between the first image or signal and the second image or signal to give a differential image or signal.
2. The method according to claim 1, wherein photochemically perturbing the material comprises photochemically perturbing the material via irradiating the material with additional radiation.

3. The method according to claim 1, wherein photochemically perturbing the material comprises photochemically perturbing the material via irradiating the material with additional radiation having the first wavelength.

4. The method according to claim 2, wherein photochemically perturbing the material comprises photochemically perturbing the material via irradiating the material with additional radiation having a second wavelength.

5. The method according to claim 2, wherein the first image or signal is a first fluorescent image and the second image or signal is a second fluorescent image.

6. The method according to claim 2, wherein the first image or signal is a first optical signal and the second image or signal is a second optical signal.

7. The method according to claim 4, wherein the additional radiation having the second wavelength is produced by a laser.

8. The method according to claim 4, wherein the additional radiation having the second wavelength is ultraviolet (UV) radiation.

9. The method according to claim 4, wherein the second wavelength is in the range 150 nm to 250 nm.

10. The method according to claim 4, wherein the second wavelength is in the range 193 nm to 213 nm.

11. The method according to claim 7, wherein the laser is an ArF excimer laser.

12. The method according to claim 11, wherein the second wavelength is about 193 nm.

13. The method according to claim 7, wherein the laser is a KrF excimer laser.

14. The method according to claim 13, wherein the second wavelength is about 248 nm.

15. The method according to claim 7, wherein the laser is a tunable Ti-Sapphire laser.

16. The method according to claim 7, wherein the laser is a tunable OPO laser.

17. The method according to claim 15, wherein the tunable Ti-Sapphire laser is tuned to a wavelength that couples to the material.

18. The method according to claim 16, wherein the tunable OPO laser is tuned to a wavelength that couples to the material.

19. The method according to claim 4, wherein the first wavelength is about 355 nm.

20. The method according to claim 7, wherein the laser is a quintupled Nd:YAG laser.

21. The method according to claim 20, wherein the second wavelength is about 213 nm.

22. The method according to claim 2, wherein the material comprises a biological tissue.

23. The method according to claim 2, wherein the material comprises a chemical sample.

24. The method according to claim 5, wherein the material comprises a biological tissue.

25. The method according to claim 5, wherein the material comprises a chemical sample.

26. The method according to claim 2, wherein photochemically perturbing the material comprises photochemically perturbing the material with a multi-photon process.

27. The method according to claim 26, wherein the multi-photon process comprises subjecting the material to radiation from at least one pulse from a femtosecond laser or ultrashort laser pulse.

28. The method according to claim 6, wherein the first optical signal comprises a series of fluorescence signals.

29. The method according to claim 6, wherein the first optical signal comprises at least one fluorescence lifetime signal.

30. The method according to claim 6, wherein the first optical signal comprises at least one Raman scattering signal.

31. The method according to claim 6, wherein the first optical signal comprises at least one multi-photon fluorescence signal.

32. The method according to claim 6, wherein the first optical signal comprises at least one photofragmentation signal.

33. The method according to claim 6, wherein the first optical signal comprises at least one light scattering or reflectivity signal.

34. The method according to claim 6, wherein the first optical signal comprises a plurality of fluorescence signals, wherein at least two of the plurality of fluorescence signals comprise different fluorescence spectral bandwidths.

35. The method according to claim 6, wherein the first optical signal is a combination of two or more of the following:
   a fluorescence signal;
   a series of fluorescence signals;
   a fluorescence lifetime signal;
   a series of fluorescence lifetime signals;
   a Raman scattering signal;
   a series of Raman scattering signals;
   a multi-photon fluorescence signal;
   a series of multi-photon fluorescence signals;
   a photofragmentation signal;
   a series of photofragmentation signals;
   a light scattering or reflectivity signal; and
   a series of light scattering or reflectivity signals.

36. The method according to claim 2, wherein photochemically perturbing the material comprises photochemically perturbing labeled or artificial chromophores.

37. The method according to claim 24, further comprising:
   utilizing the differential image or signal to detect material properties of the biological tissue.

38. The method according to claim 24, further comprising:
   utilizing the differential image or signal to detect cancer in the biological tissue.

39. The method according to claim 24, further comprising:
   utilizing the differential image or signal to detect biological contaminants.

40. The method according to claim 2, further comprising:
   utilizing the differential image or signal to detect explosive compounds.

41. A system for imaging or sensing a material, comprising:
   a radiation source, wherein the radiation source is adapted to irradiate a material with radiation having a first wavelength;
   a detector, wherein the detector is adapted to record a first image or signal from the material after the material is irradiated with the radiation having the first wavelength;
   a perturbing mechanism, wherein the perturbing mechanism is adapted to photochemically perturb the material after the detector records the first image or signal;
   wherein the radiation source is adapted to irradiate the material with radiation having the first wavelength after the material is photochemically perturbed;
   wherein the detector is adapted to record a second image or signal from the material after the material is irradiated with the radiation having the first wavelength after the material is photochemically perturbed; and a computer processor adapted to determine a difference between the first image or signal and the second image or signal to give a differential image or signal.

42. The method according to claim 1, wherein the first image or signal is a first image and the second image or signal is a second image.

43. The method according to claim 1, wherein the first image or signal is a first signal and the second image or signal is a second signal.

44. The method according to claim 1, wherein the first image or signal is a first image and the second image or signal is a second image.

45. The method according to claim 1, wherein the first image or signal is a first signal and the second image or signal is a second signal.

46. The system according to claim 41, wherein the perturbing mechanism is adapted to photochemically perturb the material via irradiating the material with additional radiation after the detector records the first image or signal.

47. The system according to claim 41, wherein the perturbing mechanism is adapted to photochemically perturb the material via irradiating the material with additional radiation at the first wavelength after the detector records the first image or signal.

48. The system according to claim 46, wherein the perturbing mechanism is adapted to photochemically perturb the material via irradiating the material with additional radiation at a second wavelength after the detector records the first image or signal.

49. The system according to claim 46, wherein the first image or signal is a first fluorescent image and the second image or signal is a second fluorescent image.

50. The system according to claim 46, wherein the first image or signal is a first optical signal and the second image or signal is a second optical signal.

51. The system according to claim 48, wherein the additional radiation having the second wavelength is produced by a laser.

52. The system according to claim 48, wherein the additional radiation having the second wavelength is ultraviolet (UV) radiation.

53. The system according to claim 48, wherein the second wavelength is in the range 150 nm to 250 nm.

54. The system according to claim 48, wherein the second wavelength is in the range 193 nm to 213 nm.

55. The system according to claim 51, wherein the laser is an ArF excimer laser.

56. The system according to claim 55, wherein the second wavelength is about 193 nm.

57. The system according to claim 51, wherein the laser is a KrF excimer laser.

58. The system according to claim 57, wherein the second wavelength is about 248 nm.

59. The system according to claim 51, wherein the laser is a tunable Ti-Sapphire laser.

60. The system according to claim 51, wherein the laser is a tunable OPO laser.

61. The system according to claim 59, wherein the tunable Ti-Sapphire laser is tuned to a wavelength that couples to the material.

62. The system according to claim 60, wherein the tunable OPO laser is tuned to a wavelength that couples to the material.

63. The system according to claim 48, wherein the first wavelength is about 355 nm.

64. The system according to claim 51, wherein the laser is a quintupled Nd:YAG laser.

65. The system according to claim 64, wherein the second wavelength is about 213 nm.

66. The system according to claim 46, wherein the perturbing mechanism is adapted to photochemically perturb the material with a multi-photon process after the detector records the first image or signal.

67. The system according to claim 66, wherein the multi-photon process comprises subjecting the material to radiation from at least one pulse from a femtosecond laser or ultrashort laser pulse.

68. The system according to claim 50, wherein the first optical signal comprises a series of fluorescence signals.

69. The system according to claim 50, wherein the first optical signal comprises at least one fluorescence lifetime signal.

70. The system according to claim 50, wherein the first optical signal comprises at least one Raman scattering signal.

71. The system according to claim 50, wherein the first optical signal comprises at least one multi-photon fluorescence signal.

72. The system according to claim 50, wherein the first optical signal comprises at least one photofragmentation signal.

73. The system according to claim 50, wherein the first optical signal comprises at least one light scattering or reflectivity signal.

74. The system according to claim 50, wherein the first optical signal comprises a plurality of fluorescence signals, wherein at least two of the plurality of fluorescence signals comprise different fluorescence spectral bandwidths.

75. The system according to claim 50, wherein the first optical signal is a combination of two or more of the following:
   a fluorescence signal;
   a series of fluorescence signals;
   a fluorescence lifetime signal;
   a series of fluorescence lifetime signals;
   a Raman scattering signal;
   a series of Raman scattering signals;
   a multi-photon fluorescence signal;
   a series of multi-photon fluorescence signals;
   a photofragmentation signal;
   a series of photofragmentation signals;
   a light scattering or reflectivity signal; and
   a series of light scattering or reflectivity signals.

76. The system according to claim 46, wherein the perturbing mechanism is adapted to photochemically perturb labeled or artificial chromophores.

77. The system according to claim 49, wherein the computer processor is adapted to utilize the differential image or signal to detect material properties of a biological tissue.

78. The system according to claim 49, wherein the computer processor is adapted to utilize the differential image or signal to detect cancer in the biological tissue.

79. The system according to claim 49, further comprising: the differential image or signal to detect biological contaminants.

80. The system according to claim 46, further comprising: the differential image or signal to detect explosive compounds.

* * * * *